(12) United States Patent
Rotella et al.

(10) Patent No.: US 10,821,224 B2
(45) Date of Patent: Nov. 3, 2020

(54) SHAPED ELASTOMERIC INFUSION PUMP

(71) Applicant: Avent, Inc., Alpharetta, GA (US)

(72) Inventors: John Anthony Rotella, San Diego, CA (US); Angela Christine Montijo, La Jolla, CA (US); Courtney E. Rowe, Marietta, GA (US); Michael A. Kenowski, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 207 days.

(21) Appl. No.: 15/744,417

(22) PCT Filed: Jul. 21, 2015

(86) PCT No.: PCT/US2015/041247
§ 371 (c)(1),
(2) Date: Jan. 12, 2018

(87) PCT Pub. No.: WO2017/014750
PCT Pub. Date: Jan. 26, 2017

(65) Prior Publication Data
US 2018/0200428 A1 Jul. 19, 2018

(51) Int. Cl.
*A61M 5/152* (2006.01)
*A61M 5/142* (2006.01)
*F04B 43/00* (2006.01)

(52) U.S. Cl.
CPC ......... *A61M 5/152* (2013.01); *A61M 5/14244* (2013.01); *A61M 2205/586* (2013.01); *F04B 43/0009* (2013.01)

(58) Field of Classification Search
CPC .................. A61M 5/152; A61M 5/14244
See application file for complete search history.

(56) References Cited

U.S. PATENT DOCUMENTS

| | | | |
|---|---|---|---|
| 3,319,684 A | * | 5/1967 | Calhoun ................ A61J 1/05 604/326 |
| 4,318,400 A | | 3/1982 | Peery et al. |
| 4,419,096 A | | 12/1983 | Leeper et al. |
| 4,646,781 A | | 3/1987 | McIntyre et al. |
| 4,769,008 A | * | 9/1988 | Hessel ................ A61M 5/152 222/211 |
| 4,813,937 A | | 3/1989 | Vaillancourt |

(Continued)

FOREIGN PATENT DOCUMENTS

WO WO 92/16304 10/1992

OTHER PUBLICATIONS

International Search Report for PCT/US2015/041247, dated Apr. 11, 2016, 3 pages.

*Primary Examiner* — Laura A Bouchelle
(74) *Attorney, Agent, or Firm* — Dority & Manning, P.A.

(57) ABSTRACT

The present invention is directed to a portable apparatus for dispensing a liquid under pressure at a substantially constant flow rate over a period of time. The apparatus includes an inflatable, internal bladder constructed of a compliant, elastomeric material and an external housing surrounding the internal bladder. Further, the external housing is constructed of a non-compliant, elastomeric material. Thus, during operation, the external housing shapes the internal bladder as the internal bladder is being filled with a treatment fluid and collapses as the treatment fluid is emptied from the internal bladder.

16 Claims, 5 Drawing Sheets

(56) References Cited

U.S. PATENT DOCUMENTS

| | | | |
|---|---|---|---|
| 4,909,790 | A | 3/1990 | Tsujikawa et al. |
| 5,006,050 | A | 4/1991 | Cooke et al. |
| 5,019,047 | A | 5/1991 | Kriesel |
| 5,041,094 | A | 8/1991 | Perego et al. |
| 5,053,031 | A | 10/1991 | Borsanyi |
| 5,080,652 | A | 1/1992 | Sancoff et al. |
| 5,105,983 | A | 4/1992 | Sancoff et al. |
| 5,137,175 | A * | 8/1992 | Kowalski ............ B65D 77/067 222/1 |
| 5,263,940 | A | 11/1993 | Kriesel |
| 5,284,481 | A | 2/1994 | Soika et al. |
| 5,306,257 | A | 4/1994 | Zdeb |
| 5,398,850 | A | 3/1995 | Sancoff et al. |
| 7,341,572 | B2 * | 3/2008 | Bridle ................... A61M 5/152 604/153 |
| 7,704,230 | B2 | 4/2010 | Chatlynee et al. |
| 9,511,188 | B2 | 12/2016 | Chi et al. |
| 2004/0171987 | A1 | 9/2004 | Bridle et al. |
| 2006/0229558 | A1 | 10/2006 | Heston et al. |
| 2008/0183135 | A1 | 7/2008 | Forrest |
| 2014/0025039 | A1 * | 1/2014 | Rajendran .......... A61B 17/3401 604/512 |

\* cited by examiner

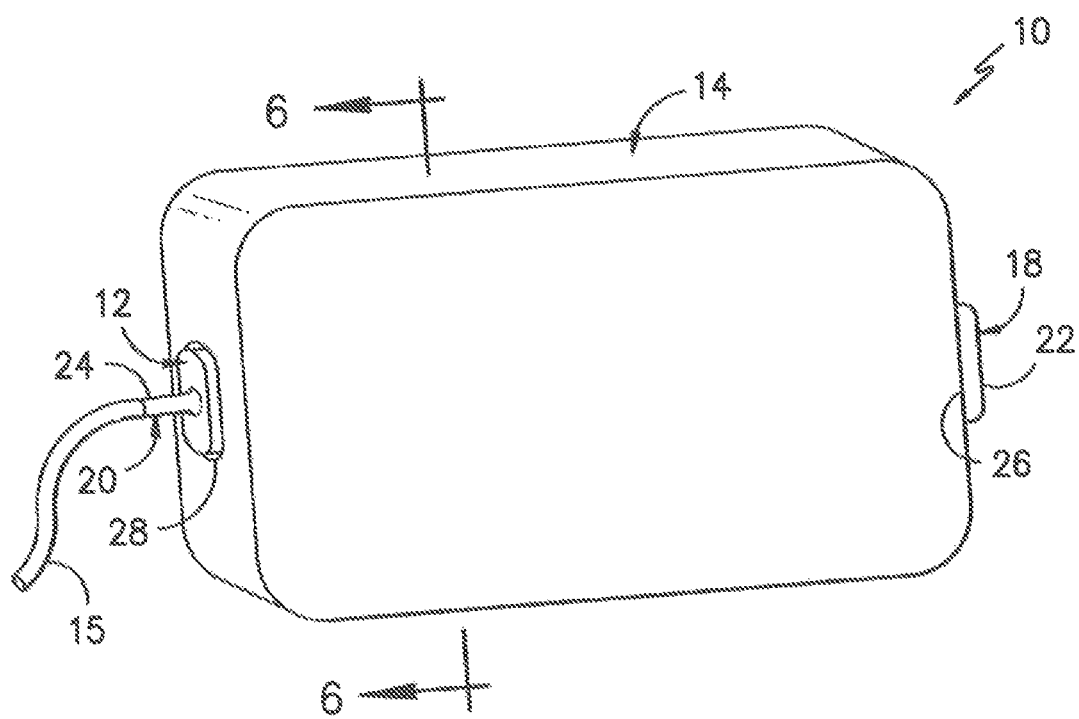
FIG. -1-
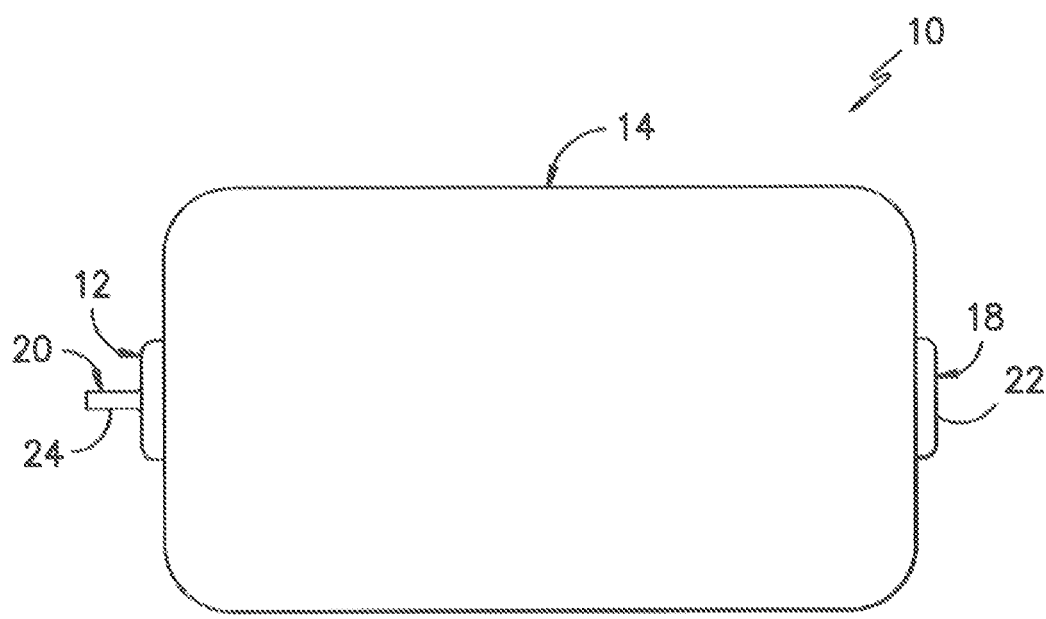
FIG. -2-

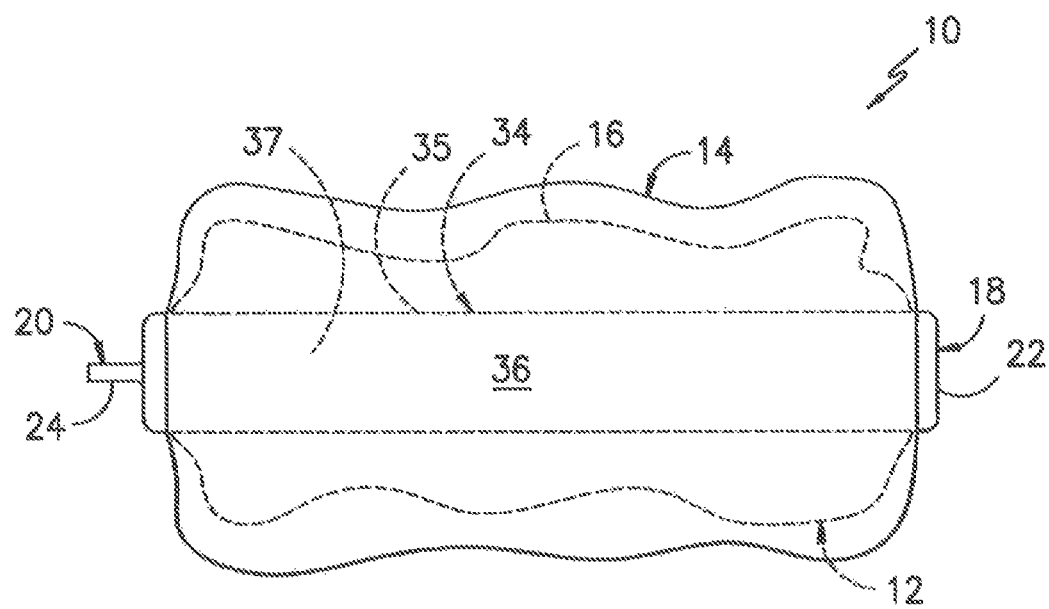
FIG. -3-
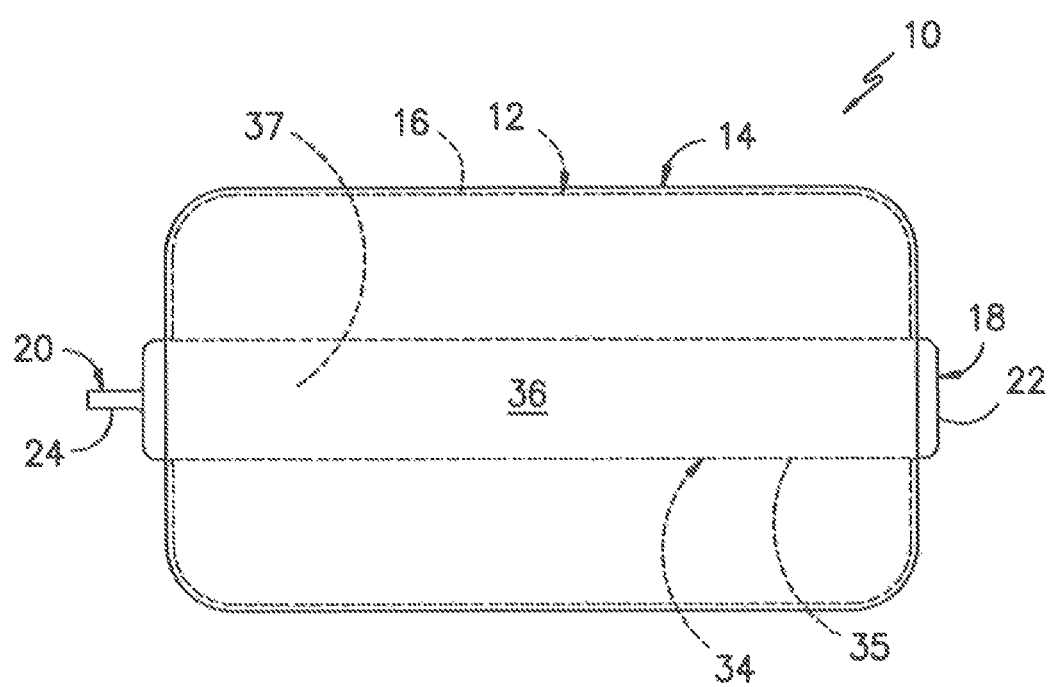
FIG. -4-

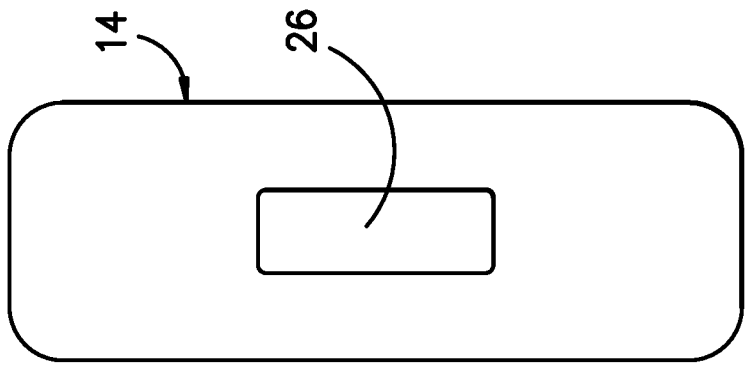
FIG. -7-
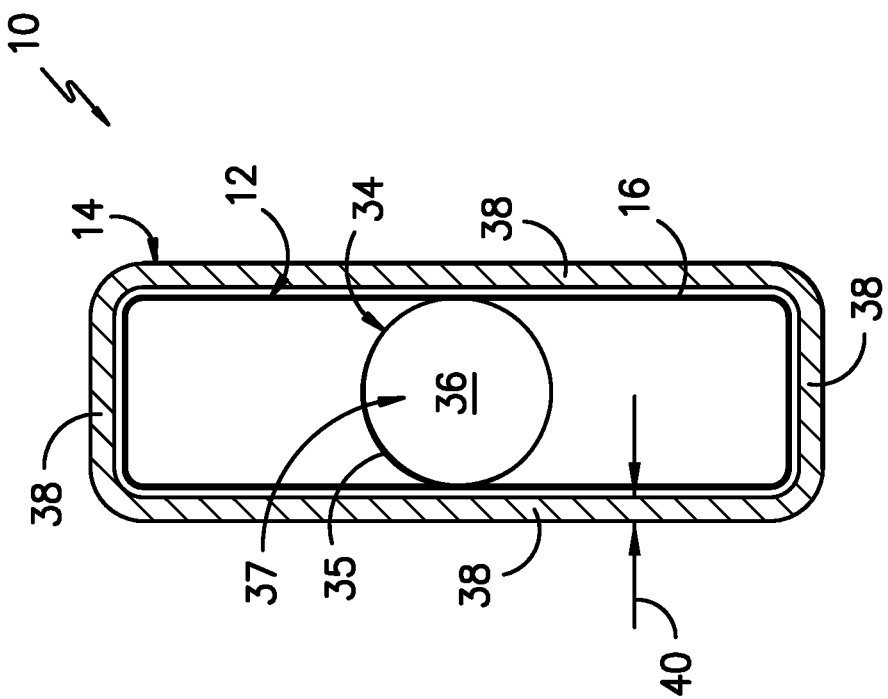
FIG. -6-
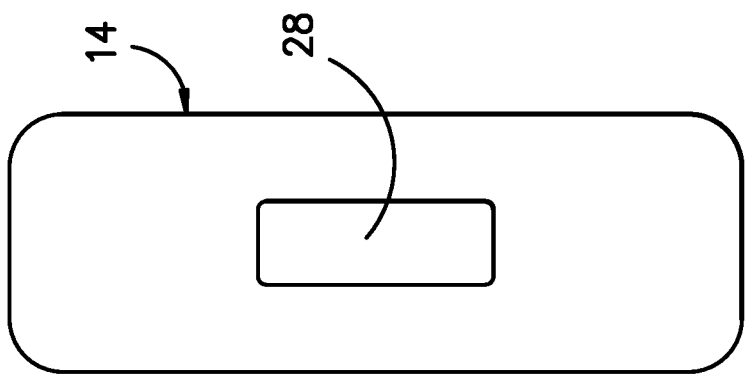
FIG. -5-

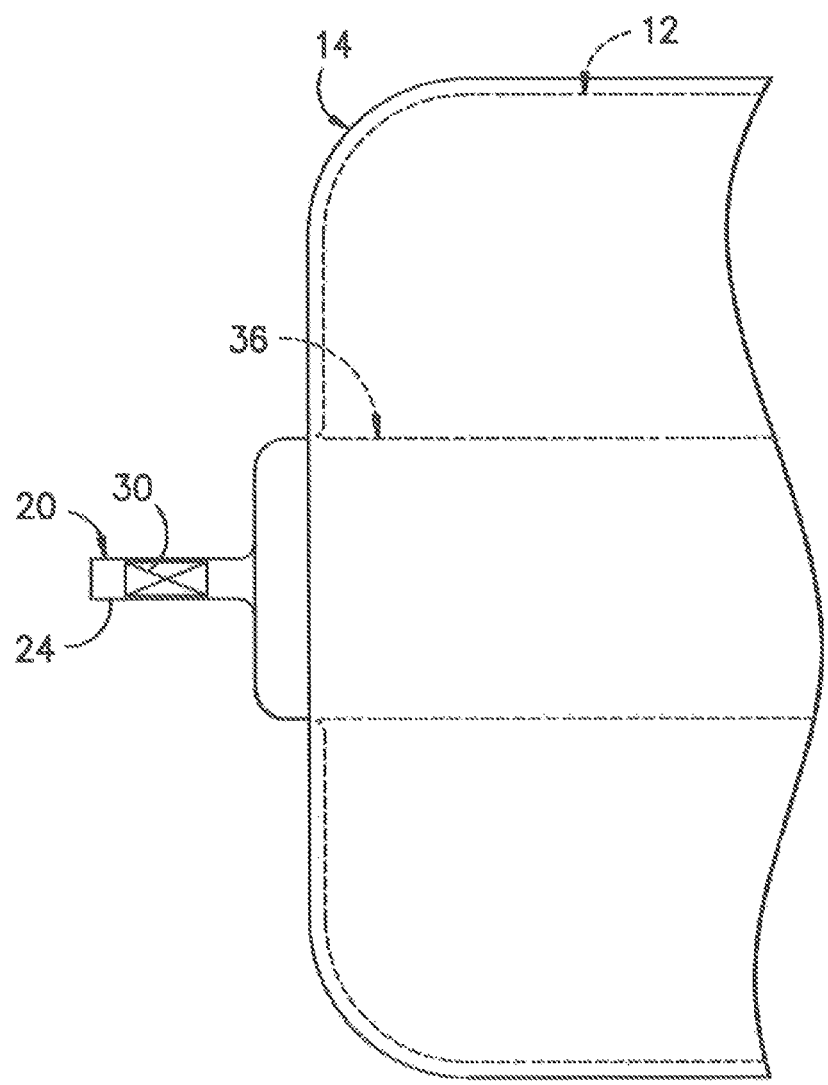
FIG. -8-

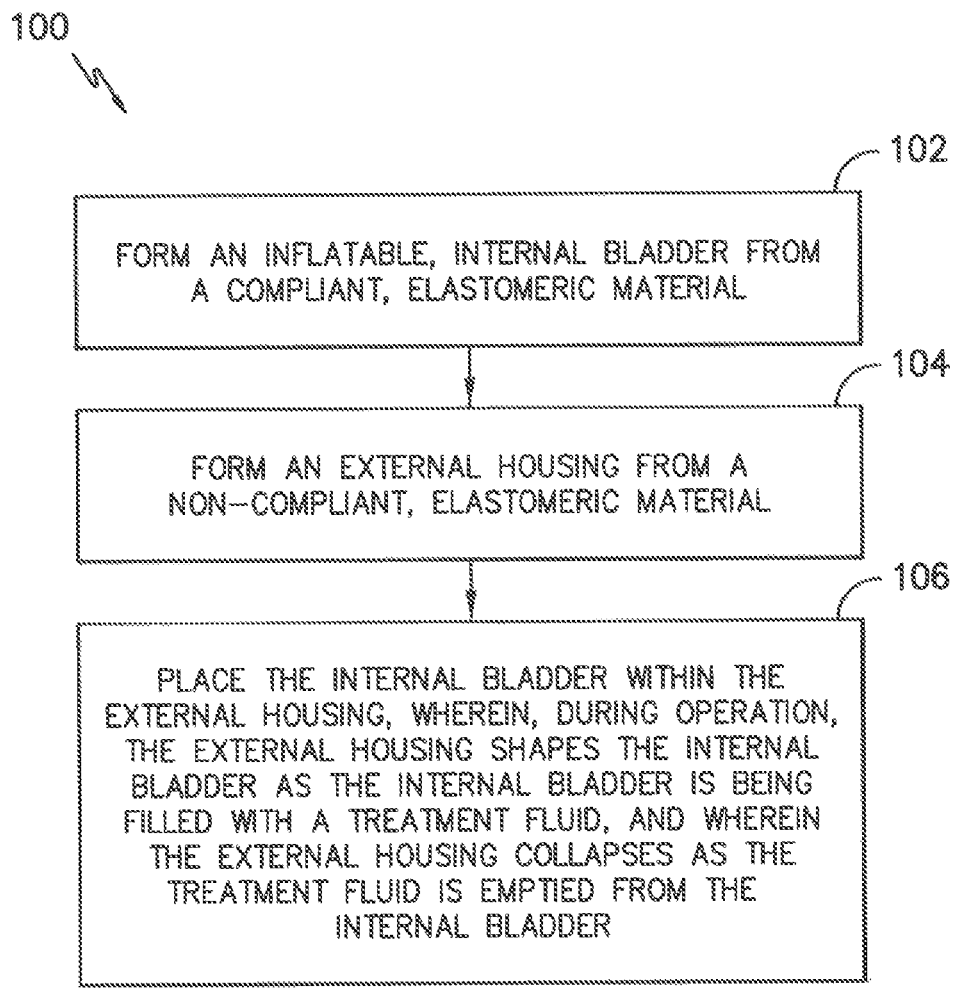
FIG. -9-

SHAPED ELASTOMERIC INFUSION PUMP

RELATED APPLICATIONS

The present application claims priority to International Application Number PCT/US2015/041247 filed on Jul. 21, 2015, which is incorporated herein in its entirety by reference hereto.

FIELD OF THE INVENTION

The present invention relates generally to a liquid dispensing apparatus for delivering intravenous drugs, and more particularly to a shaped elastomeric infusion pump that increases patient comfort.

BACKGROUND

It is often necessary to intravenously supply patients with pharmaceutically active liquids at a controlled rate over a long period of time. It is desirable that this be accomplished while the patient is in an ambulatory state. A few devices have been developed in the past for accomplishing this purpose.

The prior art devices typically include an inflatable elastomeric bladder forming a liquid container and have a flow control valve or device and tubing for supply of the liquid to the patient. The walls of the bladder are forced to expand when filled with the liquid, and provide the pressure for expelling the liquid. These prior art devices are typically filled by hand by means of a syringe which often require an inordinate amount of force.

Another drawback to the prior art devices is that the conventional inflatable elastomeric bladder provides pressures and flow rates that can vary widely with the volume of liquid therein. Therefore, they do not have a reasonably stable pressure and flow rate over the infusion period. In addition, such conventional bladders frequently have difficulty dispensing substantially all of the liquid by the end of the infusion period. It is undesirable to have liquid remaining in the bladder.

Various materials are used for constructing conventional inflatable elastomeric bladders. For example, natural rubber is frequently used. Some construction requires several layers of material. The use of silicone in tube form to function as a pressurized liquid reservoir for infusion purposes is described in, for example, U.S. Pat. No. 4,909,790 which discloses an infusion device that uses tubular bladders mounted on mandrel supports with downstream restrictors to deliver uniform flow rates. Another example may be found in U.S. Pat. No. 7,704,230 which describes a pressurized fluid reservoir made from a silicone tube for an infusion system. Such references point to numerous possible combinations of silicones, structural dimensions, filling pressures, operating pressures, and fill volumes. However, the performance provided by the silicone tube disclosed in U.S. Pat. No. 7,704,230 has been found to be unacceptable for use at least because of the variability in flow rate and the pressure during the infusion period and the difficulty dispensing substantially all of the liquid by the end of the infusion period.

In addition, many infusion pumps include hard cases (e.g. constructed of polycarbonate or similar) with an elastomeric bladder (e.g., constructed of latex, silicone, or similar) inside, which can be uncomfortable for the patient to wear, particularly while sleeping. Alternatively, additional infusion pumps may include soft cases (e.g. constructed of polyvinyl chloride (PVC) or similar) with an elastomeric bladder inside. Such infusion pumps expand spherically and can also be uncomfortable for the patient. Thus, the shape of the elastomeric bladder can be difficult to modify or control when the bladder is filled with a liquid.

Thus, the present disclosure is directed to a shaped elastomeric infusion pump that addresses the aforementioned issues.

SUMMARY OF THE INVENTION

Objects and advantages of the invention will be set forth in part in the following description, or may be obvious from the description, or may be learned through practice of the invention.

In one aspect, the present invention is directed to a portable apparatus for dispensing a liquid under pressure at a substantially constant flow rate over a period of time. The apparatus includes an inflatable, internal bladder constructed of a compliant, elastomeric material and an external housing surrounding the internal bladder. Further, the external housing is constructed of a non-compliant, elastomeric material. Thus, during operation, the external housing shapes the internal bladder as the internal bladder is being filled with a treatment fluid and collapses as the treatment fluid is emptied from the internal bladder.

In one embodiment, the internal bladder may include a support member and an elastic sleeve mounted to and surrounding the support member. Further, the support member may include a first end and an opposing second end. In further embodiments, at least one of the first or second ends may include a fill port configured for fluid communication with a fluid delivery device while the other end may include an exit port configured for fluid communication with a patient. More specifically, in one embodiment, the first end may include the fill port and the second end may include the exit port e.g. that may be connected to a catheter. Thus, in certain embodiments, the support member of the internal bladder may include a central bore defining a fluid passageway that extends from the first end to the second end.

In additional embodiments, the exit port may include a flow restrictor configured to provide a substantially constant flow rate over a predetermined period of time. For example, in certain embodiments, the flow rate may range from about 0.1 milliliters per hour (mL/hr) to about 250 mL/hr. In further embodiments, the flow range may be controlled to a range below 0.1 mL/hr or above 250 mL/hr.

In specific embodiments, the compliant, elastomeric material of the internal bladder may include silicone, latex, rubber, or similar. In particular embodiments, the non-compliant, elastomeric material of the external housing may include at least one of nylon, Kevlar, polyurethane, polyethylene terephthalate (PET), or other thermoplastic elastomers.

In addition, the external housing may have a predetermined three-dimensional shape when filled to capacity, e.g. with a treatment fluid. More specifically, the three-dimensional shape may include a plurality of side walls. Further, the side walls may be formed from an integral piece of material having a certain thickness. Moreover, in particular embodiments, the thickness may range from about 0.01 millimeter (mm) to about 0.15 millimeters. More specifically, in certain embodiments, the side wall thickness may range from about 0.04 mm to about 0.12 mm.

In additional embodiments, the three-dimensional shape of the external housing may be a generally rectangular shape. Thus, in certain embodiments, the external housing may be constructed of a single piece, thin-walled, shaped bag without elasticity. In further embodiments, the elastic sleeve of the internal bladder may include a shape that corresponds to the three-dimensional shape of the external housing when filled to full capacity. As such, as the apparatus is filled with a liquid, the external housing shapes the internal bladder. In addition, the external housing collapses as the liquid is emptied from the internal bladder, thereby providing increased comfort to a patient.

In yet another aspect, the present disclosure is directed to a method for manufacturing a portable apparatus for dispensing a liquid under pressure at a substantially constant flow rate over a period of time. The method includes forming an inflatable, internal bladder from a compliant, elastomeric material. Another step includes forming an external housing from a non-compliant, elastomeric material. The method also includes placing the internal bladder within the external housing. Thus, during operation, the external housing shapes the internal bladder as the internal bladder is being filled with a treatment fluid and collapses as the treatment fluid is emptied from the internal bladder. It should also be understood that the portable apparatus may be further configured to include any of the additional features as described herein.

In one embodiment, the step of forming the internal bladder may further include forming a support member and an elastic sleeve and placing the elastic sleeve around the support member. Further, the support member has a first end and an opposing second end. Thus, at least one of the first or second ends includes a fill port configured for fluid communication with a fluid delivery device and the other end includes an exit port configured for fluid communication with a patient. For example, in certain embodiments, the first end may include the fill port and the second end may include the exit port. In another embodiment, the step of forming the internal bladder may also include forming a central bore within the support member so as to define a fluid passageway extending from the first end to the second end.

In additional embodiments, the method may also include forming the external housing so as to have a three-dimensional shape when filled to capacity with a treatment fluid. Further, the three-dimensional shape may include a plurality of side walls formed from an integral piece of material. The method may also include forming the internal bladder so as to have a shape corresponding to the three-dimensional shape of the external housing. Thus, the shape of the internal bladder may include a fluid passageway extending from the first end to the second end. In addition, the three-dimensional shape of the external housing may include a generally rectangular shape.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of a portable apparatus for dispensing a treatment fluid according to the present disclosure, particularly illustrating the external housing of the portable apparatus inflated to full capacity;

FIG. 2 illustrates an elevation view of one embodiment of a portable apparatus for dispensing a treatment fluid according to the present disclosure, particularly illustrating the external housing of the portable apparatus inflated to full capacity;

FIG. 3 illustrates an elevation view of one embodiment of a portable apparatus for dispensing a treatment fluid according to the present disclosure, particularly illustrating the portable apparatus deflated;

FIG. 4 illustrates an elevation view of one embodiment of a portable apparatus for dispensing a treatment fluid according to the present disclosure, particularly illustrating the internal bladder of the portable apparatus inflated to full capacity;

FIG. 5 illustrates an end view of the portable apparatus of FIG. 1;

FIG. 6 illustrates a cross-sectional view of the portable apparatus of FIG. 1 along line 6-6;

FIG. 7 illustrates an opposing end view of the portable apparatus of FIG. 1;

FIG. 8 illustrates a detailed, partial view of the portable apparatus of FIG. 4, particularly illustrating the exit port of the internal bladder having a flow restrictor; and FIG. 9 illustrates a flow diagram of one embodiment of a method for manufacturing a portable apparatus for dispensing a liquid under pressure at a substantially constant flow rate over a period of time according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Generally, the present disclosure is directed to a portable apparatus, e.g. an infusion pump, for dispensing a liquid under pressure at a substantially constant flow rate over a period of time. The apparatus includes an inflatable, internal bladder constructed of a compliant, elastomeric material and an external housing surrounding the internal bladder. Further, the external housing is constructed of a non-compliant, elastomeric material. Thus, during operation, the external housing shapes the internal bladder as the bladder is being filled with a treatment fluid by forcing the internal bladder to fill up and conform to the shape of the external housing. In addition, the external housing is capable of collapsing as the treatment fluid is emptied from the internal bladder, thereby improving patient comfort.

Referring now to the drawings, FIGS. 1-8 illustrate various views of a portable apparatus 10, e.g. an infusion pump, for dispensing a treatment fluid according to the present disclosure. As shown, the portable apparatus 10 includes inflatable, internal bladder 12 housed within an external housing 14. More specifically, as shown in FIGS. 3 and 4, the internal bladder 12 may include body 16 having an elongated support member 34 and an elastic sleeve 35 mounted around the support member 34. For example, as shown, the support member 34 may be an elongated, generally cylindrical mandrel within the housing 14 and may have opposite ends (e.g. first end 18 and second end 20) exposed to the exterior of the housing 14. In addition, the elastic sleeve 35 may be sealingly clamped at opposite ends thereof around the ends 18, 20 of the support member 34. Further, as shown, the support member 34 may include a central bore 36 that defines a fluid passageway 37 extending from the first end 18 to the second end 20. In additional embodiments, at least one of the first or second ends 18, 20 may include a fill port 22 configured for fluid communication with a fluid delivery device (not shown). Thus, the other or opposite end 18, 20 may include an exit port 24 configured for fluid communication with a patient. For example, as shown generally in the figures, the first end 18 includes the fill port 22, whereas the second end 20 includes the exit port 24. It should also be understood that the fill port 22 and the exit port 24 may be located at any suitable location on the apparatus 10, including for example, the same side of the apparatus 10 rather than on opposite sides as shown. In additional embodiments, as shown in FIG. 8, the exit port 24 may also include a flow restrictor 30 configured to provide a substantially constant flow rate over a period of time. For example, in certain embodiments, the flow rate may range from about 0.1 milliliters per hour (mL/hr) to about 250 mL/hr. In specific embodiments, the flow range may be controlled to a range below 0.1 mL/hr or above 250 mL/hr.

Referring now to FIGS. 1-2 and 4-7, the external housing 14 may include a three-dimensional shape when filled to capacity with the treatment fluid. It should be understood that the three-dimensional shape of the external housing 14 may be any suitable shape such that the portable apparatus 10 is comfortable when being worn by a patient. For example, as shown in the depicted embodiments, the three-dimensional shape of the external housing 14 may be a generally rectangular shape. Thus, in such embodiments, the rectangular housing 14 can be designed with a relatively thin dimensions (e.g. width) such that the apparatus 10 can be easily placed flat against a patient, e.g. a patient's abdomen. Accordingly, the shape of the external housing 14 is configured to maximize comfort while being worn by a patient, e.g. while sleeping.

In addition, as shown in FIG. 6, the three-dimensional rectangular shape may include a plurality of side walls 38. In certain embodiments, the side walls 38 of the external housing 14 may be formed from an integral piece of material having a certain thickness 40. For example, in particular embodiments, the thickness 40 of the side walls 38 may range from about 0.01 millimeter (mm) to about 0.15 millimeters. More specifically, in certain embodiments, the side wall thickness 40 may range from about 0.04 mm to about 0.12 mm. Thus, in certain embodiments, the external housing 14 may be a single piece, thin-walled, shaped bag without elasticity. In addition, as shown in FIGS. 5 and 7, one or more of the side walls 38 may include one or more openings (e.g. first and second openings 26, 28) that are configured to receive the fill port 22 and/or the exit port 24 of the internal bladder 12. Thus, the ports 22, 24 are easily accessible from outside of the housing 14. In further embodiments, the internal bladder 12 may include a generally rectangular body (when at full capacity) that corresponds to the generally rectangular shape of the external housing 14.

In addition, the internal bladder 12 or balloon may be constructed of a compliant, elastomeric material. For example, in specific embodiments, the compliant internal bladder 12 may be constructed of silicon, latex, or similar. Further, the term "compliant" when used to describe a material as described herein is generally understood to encompass, e.g. low-pressure bladders or balloons having a shape which can expand several times its original size during use. Thus, compliant balloons typically cannot be inflated to precise dimensions or retain well defined shapes and/or high pressures.

In contrast, the external housing 14 may be constructed of a non-compliant, elastomeric material. Thus, the non-compliant external housing 14 can be constructed of a desired shape such that the housing 14 can shape the compliant internal bladder 12. For example, in particular embodiments, the non-compliant, elastomeric material of the external housing 14 may include nylon, Kevlar, polyurethane, polyethylene terephthalate (PET), or other thermoplastic elastomers. As used herein, a "non-compliant" balloon or housing is generally understood to encompass a housing that can be molded to its inflated geometry from non-compliant or low-compliant materials such that the housing retains its designed size and shape even under high pressure. Thus, the non-compliant external housing 14 is generally thin-walled and exhibits high tensile strength with relatively low elongation.

By surrounding the compliant internal bladder 12 with the non-compliant external housing 14, the external housing 14 is configured to shape the internal bladder 12 as the bladder 12 is being filled with a treatment fluid. In addition, the external housing 14 is configured to collapse as the treatment fluid is emptied from the internal bladder 12. Thus, the non-compliant housing 14 over the compliant bladder 12 provides an infusion pump that can turn into different shapes which provides increase comfort for the patient.

Referring now to FIG. 9, a flow diagram of a method 100 for manufacturing a portable apparatus for dispensing a liquid under pressure at a substantially constant flow rate over a period of time is illustrated. As shown at 102, the method 100 includes forming an inflatable, internal bladder 12 from a compliant, elastomeric material. As shown at 104, the method 100 includes forming an external housing 14 from a non-compliant, elastomeric material. As shown at 106, the method 100 includes placing the internal bladder 12 within the external housing 14. For example, in one embodiment, the internal bladder 12 may be flexible such that the bladder 12 can be collapsed and inserted into one of the first or second openings 26, 28. Thus, during operation, the external housing 14 is configured to shape the internal bladder 12 as the bladder 12 is being filled with a treatment fluid. Further, the external housing 14 is configured to collapse as the treatment fluid is emptied from the internal bladder 12.

In further embodiments, the step of forming the internal bladder 12 may further include forming a body 16 having a first end 18 and an opposing second end 20, wherein at least one of the first or second ends 18, 20 includes a fill port 22 configured for fluid communication with a fluid delivery device and the other end includes an exit port 24 configured for fluid communication with a patient. For example, in certain embodiments, the first end 18 may include the fill port 22 and the second end 20 may include the exit port 24. In another embodiment, the step of forming the internal bladder 12 may also include forming a central bore 34 within the body 16 that defines a fluid passageway 36 extending from the first end 18 to the second end 20.

In additional embodiments, the method 100 may also include forming the external housing 14 so as to have a three-dimensional shape when filled to capacity with a treatment fluid. Further, as mentioned, the three-dimensional shape may include a plurality of side walls 38 formed from an integral piece of material. Thus, the method 100 may also include forming the internal bladder 12 so as to have a shape corresponding to the three-dimensional shape of the external housing. In addition, the shape of the internal bladder 12 may include a fluid passageway 36 extending from the first end 18 to the second end 20. In addition, the three-dimensional shape of the external housing 14 may include a generally rectangular shape (as generally shown in the figures) or any other suitable shape that maximizes comfort of a patient wearing the apparatus 10.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A portable apparatus for dispensing a liquid under pressure at a substantially constant flow rate over a period of time, the apparatus comprising:
    an inflatable, internal bladder comprising a body having an elongated support member and an elastic sleeve mounted around the support member, the support member comprising a central bore defining a fluid passageway that extends from a first end to a second end of the support member, the elastic sleeve constructed, at least in part, of a compliant, elastomeric material, the compliant, elastomeric material of the elastic sleeve comprising a shape that expands as internal pressure of the internal bladder increases; and
    an external housing surrounding the internal bladder, the external housing defining a predefined, three-dimensional cuboid shape with rounded edges when filled to full capacity with the treatment fluid so as to increase patient comfort, the external housing being constructed, at least in part, of a non-compliant, elastomeric material, wherein the external housing predefined, three-dimensional cuboid shape does not expand as internal pressure of the external housing increases,
    wherein, during operation, the external housing expands to the predefined, three-dimensional cuboid shape and shapes the internal bladder to correspond to the predefined, three-dimensional cuboid shape when the internal bladder is filled with the treatment fluid to full capacity, and wherein the external housing collapses as the treatment fluid is emptied from the internal bladder.

2. The apparatus of claim 1, wherein at least one of the first or second ends comprises a fill port configured for fluid communication with a fluid delivery device, and wherein at least one of the first or second ends comprises an exit port configured for fluid communication with a patient.

3. The apparatus of claim 2, wherein the first end comprises the fill port and the second end comprises the exit port.

4. The apparatus of claim 3, wherein the exit port comprises a flow restrictor configured to provide the substantially constant flow rate over the period of time, wherein the flow rate ranges from about 0.1 milliliters per hour (mL/hr) to about 250 mL/hr.

5. The apparatus of claim 2, wherein the predefined, three-dimensional cuboid shape comprises a plurality of side walls, wherein the plurality of side walls are formed from an integral piece of material.

6. The apparatus of claim 5, wherein the plurality of side walls comprises a thickness, wherein the thickness ranges from about 0.01 millimeter (mm) to about 0.15 millimeters.

7. The apparatus of claim 1, wherein the compliant, elastomeric material of the internal bladder comprises at least one of silicone or latex.

8. The apparatus of claim 1, wherein the non-compliant, elastomeric material of the external housing comprises at least one of nylon, Kevlar, polyurethane, or polyethylene terephthalate (PET).

9. A method for manufacturing a portable apparatus for dispensing a liquid under pressure at a substantially constant flow rate over a period of time, the method comprising:
    forming an inflatable, internal bladder from a compliant, elastomeric material, the compliant, elastomeric material of the internal bladder comprising a shape that expands as internal pressure of the internal bladder increases;
    forming an external housing from a non-compliant, elastomeric material defining a predefined, three-dimensional cuboid shape having rounded edges when filled to full capacity with a treatment fluid, wherein the predefined, three-dimensional cuboid shape does not expand as internal pressure of the external housing increases; and
    placing the internal bladder within the external housing, wherein, during operation, the external housing expands to the predefined, three-dimensional cuboid shape and shapes the internal bladder to correspond to the predefined, three-dimensional cuboid shape when the internal bladder is filled with the treatment fluid to full capacity, and wherein the external housing collapses as the treatment fluid is emptied from the internal bladder.

10. The method of claim 9, wherein forming the internal bladder further comprises:
    forming a support member and an elastic sleeve, the support member having a first end and an opposing second end, and
    placing the elastic sleeve around the support member, wherein at least one of the first or second ends comprises a fill port configured for fluid communication with a fluid delivery device, and wherein at least one of the first or second ends comprises an exit port configured for fluid communication with a patient.

11. The method of claim 10, wherein the first end comprises the fill port and the second end comprises the exit port.

12. The method of claim 10, wherein forming the internal bladder further comprises forming a central bore within the support member so as to define a fluid passageway extending from the first end to the second end.

13. The method of claim 10, wherein the three-dimensional cuboid shape comprises a plurality of side walls formed from an integral piece of material.

14. The method of claim 9, wherein the compliant, elastomeric material of the internal bladder comprises at least one of silicone or latex.

15. The method of claim 9, wherein the non-compliant, elastomeric material of the external housing comprises at least one of nylon, Kevlar, polyurethane, polyethylene terephthalate (PET).

16. The method of claim 9, wherein the exit port comprises a flow restrictor configured to provide the substantially constant flow rate over the period of time, wherein the flow rate ranges from about 0.1 milliliters per hour (mL/hr) to about 250 mL/hr.

\* \* \* \* \*